(12) United States Patent
Shen et al.

(10) Patent No.: US 10,132,959 B2
(45) Date of Patent: Nov. 20, 2018

(54) THIN-LAYER SPECTROELECTROCHEMISTRY CELL AND METHODS FOR USE IN SUBTERRANEAN FORMATION OPERATIONS

(71) Applicant: Halliburton Energy Services, Inc., Houston, TX (US)

(72) Inventors: Jing C. Shen, Houston, TX (US); Dingding Chen, Tomball, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/320,951

(22) PCT Filed: Feb. 20, 2015

(86) PCT No.: PCT/US2015/016750
§ 371 (c)(1),
(2) Date: Dec. 21, 2016

(87) PCT Pub. No.: WO2016/133526
PCT Pub. Date: Aug. 25, 2016

(65) Prior Publication Data
US 2017/0205532 A1  Jul. 20, 2017

(51) Int. Cl.
*E21B 49/08* (2006.01)
*G01V 11/00* (2006.01)
(Continued)

(52) U.S. Cl.
CPC ............ *G01V 11/002* (2013.01); *E21B 49/08* (2013.01); *G01N 21/66* (2013.01); *G01N 21/78* (2013.01); *G01N 2201/061* (2013.01)

(58) Field of Classification Search
CPC ............................ G01V 11/002; E21B 49/08
See application file for complete search history.

(56) References Cited

U.S. PATENT DOCUMENTS

| 4,718,991 A | 1/1988 | Yamazoe et al. |
| 4,911,800 A | 3/1990 | Sadoway et al. |

(Continued)

FOREIGN PATENT DOCUMENTS

| CN | 102735720 A | 10/2012 |
| DE | 4332512 A1 | 3/1995 |

(Continued)

OTHER PUBLICATIONS

International Preliminary Report on Patentability from International Patent Application No. PCT/US2015/016750, dated Aug. 31, 2017, 7 pages.

(Continued)

*Primary Examiner* — Jermele M Hollington
*Assistant Examiner* — Feba Pothen
(74) *Attorney, Agent, or Firm* — Gilliam IP PLLC

(57) ABSTRACT

Apparatus, methods, and systems related to a thin-layer spectroelectrochemistry cell; electrically coupling a second end of a working electrical wire lead, a second end of a counter electrical wire lead, and a second end of a reference electrical wire lead to a potentiostat; introducing a conductive fluid into a cell body in the spectroelectrochemistry cell; introducing a detection species into the cell body; introducing a sample into the cell body; applying a voltage potential across the transparent sample window to drive an electrochemical reaction between the detection species and the sample in the transparent sample window fluid; transmitting electromagnetic radiation into an optical path through the transparent sample window, thereby optically interacting the electromagnetic radiation with the transparent sample window fluid to generate modified electromagnetic radiation; receiving the modified electromagnetic radiation with a detector; and generating an output signal corresponding to a characteristic of the sample.

20 Claims, 1 Drawing Sheet

(51) Int. Cl.
   *G01N 21/66* (2006.01)
   *G01N 21/78* (2006.01)

(56) References Cited

U.S. PATENT DOCUMENTS

| | | | |
|---|---|---|---|
| 5,451,674 | A | 9/1995 | Silver et al. |
| 5,879,949 | A | 3/1999 | Cole et al. |
| 6,015,479 | A | 1/2000 | Boss et al. |
| 6,028,025 | A | 2/2000 | Ying et al. |
| 6,821,738 | B2 | 11/2004 | Harmon |
| 7,153,532 | B1 | 12/2006 | Elsome et al. |
| 7,876,425 | B2 | 1/2011 | Sardashti et al. |
| 7,889,346 | B2 | 2/2011 | Myrick et al. |
| 7,948,041 | B2 | 5/2011 | Bryant et al. |
| 8,081,313 | B2 | 12/2011 | Lam et al. |
| 8,092,661 | B2 | 1/2012 | Canonne et al. |
| 8,345,251 | B2 | 1/2013 | Myrick et al. |
| 8,372,650 | B2 | 2/2013 | Toyoda |
| 8,585,880 | B2 | 11/2013 | Chatterjee et al. |
| 8,722,879 | B2 | 5/2014 | Van Der Boom et al. |
| 2003/0170906 | A1 | 9/2003 | Swain et al. |
| 2004/0072360 | A1 | 4/2004 | Naaman et al. |
| 2009/0314711 | A1 | 12/2009 | Barry et al. |
| 2011/0097817 | A1* | 4/2011 | Galiano .................. G01N 1/38 436/501 |
| 2011/0199102 | A1 | 8/2011 | Garcia et al. |
| 2012/0187000 | A1 | 7/2012 | Kahn et al. |
| 2013/0125618 | A1 | 5/2013 | Hiranaka et al. |
| 2013/0340518 | A1* | 12/2013 | Jones .................... E21B 49/005 73/152.55 |
| 2014/0011286 | A1 | 1/2014 | Potyrailo et al. |
| 2014/0060641 | A1 | 3/2014 | Nazeeruddin et al. |
| 2014/0069811 | A1 | 3/2014 | Newton et al. |
| 2014/0069815 | A1 | 3/2014 | Newton et al. |
| 2015/0138621 | A1 | 5/2015 | Reynolds et al. |
| 2015/0247818 | A1 | 9/2015 | Silvester et al. |

FOREIGN PATENT DOCUMENTS

| | | |
|---|---|---|
| DE | 20012374 U1 | 2/2001 |
| EP | 2019308 A2 | 1/2009 |
| ES | 2302581 A1 | 7/2008 |
| ES | 2307356 A1 | 11/2008 |
| WO | WO-2014060949 A2 | 4/2014 |
| WO | 2016133526 A1 | 8/2016 |

OTHER PUBLICATIONS

Futur, Electrochemical and Spectroelectrochemical Studies of Porphyrazines and Related Precursors, University of Houston Thesis, Dec. 2013.

Dai et al., Equilibrium and Kinetic Behavior of Fe(Cn)63-/4-and Cytochrome c in Direct Electrochemistry Using a Film Electrode Thin-Layer Transmission Cell, Anal Chem. Jan. 15, 2011; 83(2): 542-548.

Domingos et al., An optically transparent thin-layer electrochemical cell for the study of vibrational circular dichroism of chiral redox-active molecules, Review of Scientific Instruments 84, 033103 (2013).

Kato et al., Spectroelectrochemical determination of the redox potential of pheophytin a, the primary electron acceptor in photosystem II, Proceedings of the National Academy of Sciences of the USA, vol. 106 No. 41, Oct. 13, 2009.

Wilson, R., Spectroelectrochemical Sensing and Detection of Zinc in Serum by Anodic Stripping Voltammetry on a Bismuth Film Electrode, University of Cincinnati Dissertation, 2011.

Tutunea, Spectroelectrochemistry and Voltammetry of Metal-loporphinones, Marquette University Dissertation, 2011.

Noel et al., Cyclic voltammetry and the frontiers of electrochemistry, Ch. 2, p. 62-99 (1990).

Kumeria et al., "A nanoporous interferometric micro-sensor for biomedical detection of volatile sulphur compounds," Nanoscale Research Letters, 6:634 (2011).

Jean-Philippe et al., Detection of mercury and other metals in mercury contaminated soils using mid-infrared spectroscopy, Proceedings of the International Academy of Ecology and Environmental Sciences, 2012, 2(3):139-149.

Morita et al., The Determination of Mercury Species in Environmental and Biological Samples, Pure & Appl. Chem., vol. 70, No. 8, pp. 1585-1615, 1998.

Keates, Dr. R.A.B. 2004 Lecture 2, 3, 4. Chem 3560: Structure and Function in Biochemistry. Department of Chemistry and Biochemistry: University of Guelph.

Sears, D. W., Overview of Hemoglobin's Structure/Function Relationships (1999).

Collman et al., Carbon Monoxide Binding to Iron Porphyrins, Proc. Nati. Acad. Sci. USA, vol. 76, No. 12, pp. 6035-6039 (1979).

Lister et al., Optical Properties of Human Skin, J. Biomed. Opt. 17(9), 090901 (Sep. 24, 2012).

Pavlik et al., Hydrosulfide (HS-) Coordination in Iron Porphyrinates, Inorg Chem. 49(3), 1017-1026 (2010).

Perutz, Hemoglobin Structure and Respiratory Transport, Scientific American, 1978.

Tremper et al., Pulse Oximetry, Anesthesiology 70:98-100, 1989.

Kadish, The Porphyrin Handbook, 1999.

Wilhelm et al., Mercury in Crude Oil Processed in the United States (2004), Environ. Sci. Technol. 41(13), 4509 (2007).

Smith et al. "On the Synthesis of Etiporphyrin by Monopyrrole Tetramerization," J. Org. Chem. 44, 2591-2 (1979).

Dunbar et al., "Detection of Volatile Organic Compounds Using Porphyrin Derivatives," The Journal of Physical Chemistry B 2010 114 (36), 11697-11702 (2010).

Ishihara et al., Porphyrin-based sensor nanoarchitectonics in diverse physical detection modes, Phys. Chem. Chem. Phys., 2014,16, 9713-9746.

International Search Report and Written Opinion for PCT/US2015/016750 dated Oct. 30, 2015.

Larsen et al., "Hydrogen Sulfide Detection by UV-Assisted Infrared Spectrometry," Applied Spectroscopy, vol. 51, Issue 11, pp. 406A-429A an 1593-1767 (Nov. 1997), pp. 1656-1667(12).

* cited by examiner

THIN-LAYER SPECTROELECTROCHEMISTRY CELL AND METHODS FOR USE IN SUBTERRANEAN FORMATION OPERATIONS

BACKGROUND

The embodiments herein relate generally to apparatus and methods for use in subterranean formation operations and, more particularly, to spectroelectrochemical cells such as a thin-layer spectroelectrochemical cell and methods of use thereof in subterranean formation operations.

In the oil and gas industry, a drilling fluid is typically used during drilling of a wellbore to facilitate the drilling process and to maintain a hydrostatic pressure in the wellbore greater than the pressure in the subterranean formation (also referred to simply as "formation") surrounding the wellbore. This drilling fluid penetrates into or invades the formation for varying radial depths (referred to generally as the invaded zones) depending upon, among other things, the type of formation and drilling fluid used. Downhole formation testing tools lowered into the wellbore during or after drilling may be used to monitor formation pressures, collect formation fluid samples from the wellbore, to predict performance of reservoirs around the wellbore, and the like. These formation testing tools typically contain an elongated body having an elastomeric packer or pad that is sealed against a zone of interest in the wellbore. A passage or flow channel in the sealed system is used to withdraw fluid from the formation. This fluid is collected within the tool and analyzed in the wellbore or brought to the surface for analysis to determine the properties of the fluids, conditions of the formation from where the fluids were collected, and the like.

Traditionally, species in formation fluids (e.g., concentrations and/or types of species linked to the formation fluids content) are analyzed. Often, the formation fluids are analyzed using traditional spectroscopy techniques, where a spectra is obtained from the formation fluids which is correlative to a type or concentration of a particular species in the formation fluids. However, detection of particular species or a concentration thereof may be difficult where such species fail to produce strong optical signals. In such instances, the type and condition of the formation fluids and/or of reservoirs in the formation may be unattainable or only a suboptimal amount of information may be realized.

BRIEF DESCRIPTION OF THE DRAWINGS

The following figures are included to illustrate certain features and inventive aspects of the embodiments described herein, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
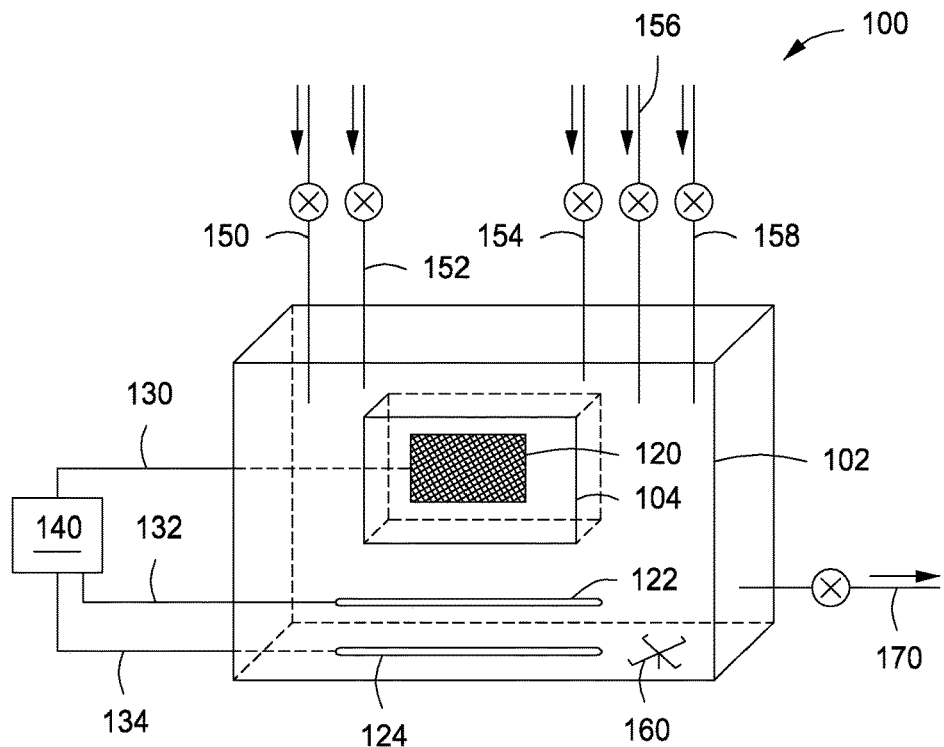
FIG. 1 depicts a thin-layer spectroelectrochemical cell according to one or more embodiments of the present disclosure.

The embodiments herein relate generally to apparatus and methods for use in subterranean formation operations and, more particularly, to spectroelectrochemical cells such as a thin-layer spectroelectrochemical cell and methods of use thereof in subterranean formation operations. A number of aspects and embodiments of the present disclosure are described below. Separate inventive features are described in the context of particular embodiments, but are not limited to only those embodiments, unless this is explicitly stated. Thin-layer spectroelectrochemical cells are disclosed, which may be combined with a source of electromagnetic radiation and a detector. The apparatus may include a potentiostat, and may include a fluid mixer. The apparatus may be integrated within or located on a downhole tool such as a formation tester during performance of a subterranean formation operation, or may be located in a fluid pipeline, such as to acquire data relating to species located downhole.

Spectroelectrochemistry couples spectroscopic and electrochemical techniques together to perform measurements and data collection of certain fluids. Specifically, spectroelectrochemistry used herein evaluates of spectra which are related individually to the type and concentrations of oxidized and/or reduced species. As used herein, the term "fluid" refers to materials in a liquid and/or gaseous phase.

Sensing a species in a fluid, such as a metal ion, using spectroelectrochemistry may have poor sensitivity due to a small difference in the molar absorptivities between the species in its reduced and oxidized states, resulting in weak optical signals. However, when a coordinating ligand serves as a strong chromophore for the reduced and/or oxidized states to complex with the metal ions, a larger difference in molar absorptivities may be achieved, thereby improving the optical signals and the detection thereof. Heightening the signal allows an operator to more fully understand the components of a particular formation fluid being tested, thereby allowing more informed decisions regarding completion and production of the formation to be made, reducing operator time and enhancing formation productivity. Other fluids may also be evaluated in a downhole location, such as treatment fluids placed therein that have interacted with the formation. In such instances, the alteration of the treatment fluid by one or more species from the formation may be detectable.

In some embodiments, the apparatuses and methods described herein may be with reference to a drilling or logging operation in a subterranean formation. However, the apparatuses and methods may be used in any other subterranean formation operation that may benefit from in-situ (or ex-situ) spectroelectrochemical measurements of fluids. These operations may also be in a subterranean formation and relate to the oil-and-gas industry, but may also pertain to operations outside of the oil-and-gas industry, without departing from the scope of the present disclosure.

One or more illustrative embodiments disclosed herein are presented below. Not all features of an actual implementation are described or shown in this application for the sake of clarity. It is understood that in the development of an actual embodiment incorporating the embodiments disclosed herein, numerous implementation-specific decisions must be made to achieve the developer's goals, such as compliance with system-related, lithology-related, business-related, government-related, and other constraints, which vary by implementation and from time to time. While a developer's efforts might be complex and time-consuming, such efforts would be, nevertheless, a routine undertaking for those of ordinary skill in the art having benefit of this disclosure.

It should be noted that when "about" is provided herein at the beginning of a numerical list, the term modifies each number of the numerical list. In some numerical listings of ranges, some lower limits listed may be greater than some upper limits listed. One skilled in the art will recognize that the selected subset will require the selection of an upper limit in excess of the selected lower limit. Unless otherwise indicated, all numbers expressing quantities of ingredients, properties such as temperature, pressure, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the exemplary embodiments described herein. At the very least, and not as an attempt to limit the application of the doctrine of equivalents to the scope of the claim, each numerical parameter should at least be construed in light of the number of reported significant digits and by applying ordinary rounding techniques.

While compositions and methods are described herein in terms of "comprising" various components or steps, the compositions and methods can also "consist essentially of" or "consist of" the various components and steps. When "comprising" is used in a claim, it is open-ended.

In some embodiments herein, a thin-layer spectroelectrochemical cell is provided that can be used in a downhole environment to acquire in-situ data regarding species in fluids located therein, the data may beneficially be gathered at real-time or substantially real-time. As mentioned previously, the tested fluids or "samples" may be formation fluid or introduced fluids that have contacted the formation. As used herein, the term "substantially" means largely, but not necessarily wholly. Various types of species may be evaluated for their presence and/or absence in a sample, as discussed in greater detail below, before, during, and/or after certain subterranean formation operations have taken place.

Referring now to FIG. 1, depicted is a thin-layer spectroelectrochemical cell 100 according to one or more embodiments of the present disclosure. As shown, the thin-layer spectroelectrochemical cell 100, alternatively referred to herein simply as "cell 100," comprises a cell body 102 that is hermetically sealed and has a first volume. As depicted, the cell body 102 is depicted as a cube or rectangular prism, any shape having a volume and allowing a transparent sample window 104 to be defined therein may be suitable, without departing from the scope of the present disclosure. Generally, the shape of the cell body 102 is preferably such that the cell body 102 has a base that can balance the cell body 102 while in operation, which may permit it to better be used in downhole tools, as discussed in detail below. It may also be preferred that the shape of the cell body 102 be symmetrical about two axes; such shapes may include, but are not limited to, a cube, a cuboid, a cylinder, a hexagonal prism, a triangular prism, and the like. However, bilateral symmetrical shapes may also be used for forming the cell body 102 without departing from the scope of the present disclosure including, but not limited to, a cone, a square-based pyramid, a rectangle-based pyramid, a triangular-based pyramid, and the like. Similarly, asymmetrical shapes or shapes that do not have a base may be selected for forming the cell body 102, without departing from the scope of the present disclosure.

In some embodiments, the cell body 102 may be made of a material capable of withstanding elevated temperatures and pressures, commonly encountered in a downhole environment. That is, at elevated temperatures and pressures, the cell body 102 remains intact and does not substantially experience structural compromise over time during a subterranean formation operation. In other embodiments, the cell body 102 may be pressure balanced such that the elevated temperatures and pressures experienced by the cell body 102 in a downhole environment are substantially eliminated and need not be controlled for.

For example, the cell body 102 may be used at temperatures in the range of a lower limit of about 0° C., 10° C., 20° C., 30° C., 40° C., 50° C., 60° C., 70° C., 80° C., 90° C., 100° C., 110° C., 120° C., 130° C., 140° C., and 150° C. to an upper limit of about 300° C., 290° C., 280° C., 270° C., 260° C., 250° C., 240° C., 230° C., 220° C., 210° C., 200° C., 190° C., 180° C., 170° C., 160° C., and 150° C., encompassing any value and subset therebetween.

In some embodiments, the cell body 102 may be used at pressures in the range of a lower limit of about 14.7 pounds per square inch (psi), 100 psi, 500 psi, 1000 psi, 2000 psi, 4000 psi, 6000 psi, 8000 psi, 10000 psi, 12000 psi, 14000 psi, 16000 psi, 18000 psi, and 20000 psi to an upper limit of about 45000 psi, 44000 psi, 42000 psi, 40000 psi, 38000 psi, 36000 psi, 34000 psi, 32000 psi, 30000 psi, 28000 psi, 26000 psi, 24000 psi, 22000 psi, and 20000 psi, encompassing any value and subset therebetween.

The operational times in which the cell 100 and cell body 102 may be exposed to downhole temperatures and pressures, such as those described above, may be any time necessary to commence and complete a particular subterranean formation operation. Such operational times may be in the range of a lower limit of about 30 minutes, 1 hour (hr), 5 hr, 10 hr, 20 hr, 40 hr, 60 hr, 80 hr, 100 hr, 120 hr, and 140 hr to an upper range of about 360 hr, 340, 320 hr, 300 hr, 280 hr, 260 hr, 240 hr, 220 hr, 200 hr, 180 hr, 160 hr, and 140 hr, encompassing any value and subset therebetween. In some instances, operational times may be even greater than 360 hours, including up to 20 days, or one month. The operational time in which the cell 100 and cell body 102 may be exposed to downhole conditions may depend on a number of factors including, for example, the type of formation evaluation tool being used, and the like. Without being limited, the following example operational times are provided for reference. For example, certain wireline tools, such as a WIRELINE DESCRIPTION TOOL (RDT™), available from Halliburton Energy Services, Inc. in Houston, Tex., may require operational times from about a few hours to about several days, typically not more than about five days (about 120 hours). Other tools, such as measurement-while-drilling tools, may require more extensive operational times, ranging from about a day or about a few days to about 15 days (360 hours). Moreover, in some instances, the sampling event itself (e.g., withdrawing and collecting formation fluid as described above) often occurs toward the bottom of a wellbore, thus requiring the cell 100 and cell body 102 to be in a downhole environment for a prolonged period of time.

The sampling event compared to the operational time may be considerably abbreviated, keyed merely to the time required to gather a sample of formation fluid. The analysis event itself (i.e., analysis using the cell 100 described herein) may or may not occur in a downhole environment, but may be later in time than the operation, particularly where the formation fluid is trapped within a tool. The analysis event typically may be completed in a range of a lower limit of about 3 seconds (sec), 5 sec, 10 sec, 30 sec, 1 minute (min), 5 min, 10 min, 20 min, 40 min, 60 min, 80 min, 100 min to an upper limit of about 300 min, 280 min, 260 min, 240 min, 220 min, 200 min, 180 min, 160 min, 140 min, 120 min, and 100 min, encompassing any value and subset therebetween. The time duration of the analysis event may depend on a number of factors including, for example, the sensitivity of the instrumentation described herein, the signal-to-noise ratio, and the like.

The temperatures, pressures, and operational times provided herein, however, are non-limiting and may depend on the type of formation, the type of cell body material selected, the means of achieving hermetic sealing selected, and the like.

In some embodiments, the cell body 102 may be composed of a material selected from the group consisting of poly(ether ketone), poly(ether ether ketone), poly(ether ketone ketone), poly(ether ether ketone ketone), poly(ether ketone ether ketone ketone), poly(methyl methacrylate), polyethylene, polypropylene, polystyrene, polyvinyl chloride, polytetrafluoroethylene, polycarbonate, polybenzimidazole, a corrosion resistant metal (e.g., titanium, titanium alloy, zirconium, niobium alloy, nickel, nickel alloy), a metal alloy (e.g., titanium alloy), a superalloy (e.g., INCONEL®, a family of austenitic nickel-chromium-based superalloys available from Special Metals Corp. of New Hartford, N.Y.), and any combination thereof. In some instances, a corrosion resistant metal, a metal alloy, or a super alloy may be preferred for forming the cell body 102. In other instances, a titanium, a titanium alloy, or INCONEL® may be preferred for forming the cell body 102.

In some embodiments, the volume of the cell body 102 may be in the range of a lower limit of about 0.02 milliliters (ml), 0.05 ml, 0.1 ml, 0.25 ml, 0.5 ml, 0.75 ml, 1 ml, 2.5 ml, 5 ml, 10 ml, 50 ml, 100 ml, 250 ml, 500 ml, 750 ml, 1000 ml, 1250 ml, 1500 ml, 1750 ml, 2000 ml, 2250 ml, and 2500 ml to an upper limit of about 5000 ml, 4750 ml, 4500 ml, 4250 ml, 4000 ml, 3750 ml, 3500 ml, 3250 ml, 3000 ml, 2750 ml, and 2500 ml, encompassing any value and subset therebetween.

The cell body 102 may be hermetically sealed, such that it possesses the quality of being impervious to fluids, including gasses. The hermetic seal may be achieved using a taper joint and a sealing device including, but not limited to, a sealing ring, o-ring, sleeve, tape, resin string, and any combination thereof. Such sealing devices may be made of any material capable of maintaining a hermetic seal in a downhole location including, for example, polytetrafluoroethylene. In other embodiments, the cell body 102 may be glued or welded, such as by resin gluing (e.g., epoxy resin), resistance welding, soldering, electron-beam welding, laser welding, screwed, interlocked, and any combination thereof. Due to the elevated temperatures and pressures that may be experienced by the cell body 102, the potential for constant fluid contact and corrosive environments, it may be preferred that the cell body 102 is welded.

A transparent sample window 104 is defined in the cell body 102 and in fluid communication therewith (e.g., using an o-ring seal). The transparent sample window 104 defines an optical path through the cell body 102. As used herein, the term "optical path" refers to the path that electromagnetic radiation takes to traverse a distance, and in this case, at least the distance through the cell body 102 defining the transparent sample window 104. The transparent sample window 104 may be composed of a variety of transparent rigid or semi-rigid materials that are configured to allow transmission of electromagnetic radiation therethrough at the wavelength of interest. In some embodiments, the material forming the transparent sample window 104 may be composed of a material including, but not limited to, glass, quartz, sapphire, fused quartz, aluminum oxide, and any combination thereof. The sample window 104 may be in any three-dimensional form, such as a cube, a rod, a disk, a prism, a cone, a cylinder, a fiber (e.g. a very narrow cylinder), or the like.

The transparent sample window 104 has a second volume that is substantially smaller than that of the cell body 102. The shape of the transparent sample window 104 is non-limiting and may include any shape discussed above with reference to the cell body 102, without departing from the scope of the present disclosure, provided that the transparent sample window is able to hold a volume of fluid at the temperature and pressure ranges discussed above and permit the transmission of electromagnetic radiation therethrough, as discussed in greater detail below.

The fluid that enters into the transparent sample window 104 (e.g., formation fluid or other fluid, such as introduced downhole fluid) may be subjected to spectroelectrochemical analysis, as discussed in greater detail below. However, the fluid in the cell body 102 and that in the transparent sample window 104 is substantially identical, although only the fluid in the transparent sample window 104 is subjected to a voltage potential, whereas the fluid in the cell body 102 remains neutral. The voltage potential, also discussed in greater detail below, drives electrochemical reactions that indicate the relative oxidized or reduced state of species within the fluids. In some embodiments, the volume of the transparent sample window 104 may be in the range of a lower limit of about 0.01 ml, 0.02 ml, 0.05 ml, 0.1 ml, 0.15 ml, 0.2 ml, 0.25 ml, 0.3 ml, 0.35 ml, 0.4 ml, 0.45 ml, and 0.5 ml to an upper limit of about 1 ml, 0.95 ml, 0.9 ml, 0.85 ml, 0.8 ml, 0.75 ml, 0.7 ml, 0.65 ml, 0.6 ml, 0.55 ml, and 0.5 ml, encompassing any value and subset therebetween.

The location of the transparent sample window 104, although shown substantially in a central location within the cell body 102 may, without departing from the scope of the present disclosure, be located at any position in fluid communication with the cell body 102, provided the fluid from the cell body 102 is able to enter and leave the transparent sample window 104 when the fluid in the cell body 102 is mixed, as discussed in greater detail below. For example, the transparent sample window 104 may be located to the left or right of the center point of the cell body 102, including abutting the side edge of the cell body 102. Moreover, the transparent sample window 104 may be located above or below the center point of the cell body 102, including abutting the bottom edge of the cell body 102. However, the transparent sample window 104 is preferably not positioned at a location abutting the top edge of the cell body 102 unless the transparent sample window 104 is configured to allow from the cell body 102 to enter and leave the transparent sample window 104 when the fluid in the cell body 102 is mixed.

The cell 100 comprises working electrode 120 extending through the cell body 102 and into the transparent sample window 104 that is hermetically sealed therethrough, a counter electrode 122 extending through the cell body 102 that is hermetically sealed therethrough, and a reference electrode 124 extending through the cell body 102 that is hermetically sealed therethrough. Each of the electrodes 120, 122, and 124 is so configured to permit a voltage potential to be formed across the transparent sample window 104, while the remaining fluid in the cell body 102 remains neutral.

In some embodiments, the working electrode 120, counter electrode 122, and reference electrode 124 (collectively "electrodes") may be electrically coupled to a first end of a working electrical wire lead 130, counter electrical wire lead 132, and reference electrical wire lead 134 (collectively "electrical wire leads"), respectively. The electrodes and electrical wire leads may extend through the cell body 102 and, in the case of the working electrode 120, the transparent sample window 104, and be hermetically sealed using any of the methods discussed previously with reference to the cell body 102 (e.g., o-rings, welding components, an epoxy, and the like), without departing from the scope of the present disclosure. In some embodiments, the electrodes and the electrical wire leads may be positioned in a tube (not shown) that extends through the cell body 102 and, which may abut or extend into the transparent sample window 104. The tube may form hermetic seals by threading through the cell body 102 and transparent sample window 104, where o-rings or other sealing mechanisms may be used to provide an airtight seal between the tube and the cell body 102.

The configuration of the working electrode 120, counter electrode 122, and reference electrode 124 relative to one another in the cell 100 is not limiting. As depicted, the working electrode 120 is positioned through the cell body 102 and into the transparent sample window 104 at a location above the counter electrode 122 and reference electrode 124, which themselves are substantially parallel. However, any other configuration may be acceptable provided that the working electrode 120 is wholly or substantially located within the transparent sample window 104 and the counter electrode 122 and reference electrode 124 are located within the cell body 102, without departing from the scope of the present disclosure. For example, the counter electrode 122 and working electrode 124 may be located above or below each other, may be located on the same or different edges (e.g., side, bottom, top) of the cell body 102 relative to each other, together above or below the working electrode 120 together, separately above and below the working electrode 120 (e.g., one above and one below), together on the same edge of the cell body 102 relative to the working electrode 120, separately on different edges of the cell body 102 relative to the working electrode 120, and the like.

In some embodiments, the working electrode 120, the counter electrode 122, and the reference electrode 124 may all or any combination thereof be at least partially (i.e., partially or fully) coated with a functional coating. The functional coating may enhance properties of the electrodes such as by, for example, functioning as a binding species for the sample or detection species described below. The functional coating may include, but is not limited to, nano-gold particles.

The electrical wire leads of each of the electrodes described herein may extend from the cell body 102 and electrically connect on a second end (the end opposite of the end connected to the electrodes) to a potentiostat 140. The potentiostat 140 may be used to establish and maintain a constant voltage potential between the working electrode 120 and the reference electrode 124, such that current flows between the working electrode 120 and the counter electrode 122. The particular voltage potential selected may depend on the requirements of the particular operation including, but not limited to, the type of sample, detection species, and the like. Generally, the voltage potential applied across the transparent sample window 104 may be in the range of a lower limit of about −2.0 volts (V), −1.8 V, −1.6 V, −1.4 V, −1.2 V, −1.0 V, −0.8 V, −0.6 V, −0.4 V, −0.2 V, −0.0 V, +0.2 V, +0.4 V, and +0.6 V to an upper limit of about +3.0 V, +2.8 V, +2.6 V, +2.4 V, +2.2 V, +2.0 V, +1.8 V, +1.6 V, +1.4 V, +1.2 V, +1.0 V, +0.8 V, and +0.6 V, encompassing any value and subset therebetween.

With reference to the working electrode 120, a "working electrode" is the electrode in an electrochemical system on which the reaction of interest occurs (e.g., reduction and oxidation of species). The working electrode 120, as depicted in FIG. 1, may be in a middle position in the transparent sample window and may be a mesh electrode electrically coupled to the end of a working electrical wire lead 130. It is understood, however, that the working electrode 120 may be other types of electrodes including, but not limited to, an ultra-microelectrode, a rotating disk electrode, a rotating ring-disk electrode, a hanging mercury drop electrode, a dropping mercury electrode, a wire electrode, a metal film electrode, a structured metal thin film electrode, and the like, without departing from the scope of the present disclosure.

The working electrical wire lead 130 may be connected to the working electrode 120 by any means suitable for providing electrical communication between the working electrical wire lead 130 and the working electrode 120. Suitable connections may include, but are not limited to soldering, an electrically conductive adhesive (e.g., epoxy), a mechanical connection (e.g., a plug, a clamp, through-hole configurations, and the like) that is insulated and hermetically sealed, and the like. The working electrical wire lead 130 may be composed of any electrically conductive material including, but not limited to, an electrically conductive metal (e.g., platinum wire, copper wire, tinned copper wire, aluminum wire, and the like). In some embodiments, the working electrical wire lead 130 may preferably be insulated by a sheath material. The sheath provides insulation such that internal electric charges do not flow freely, making it difficult to conduct an electric current under the influence of an electric field; rather, purposeful applied voltage travels through a sheathed wire. The sheath may also confer resistance to exposure to heat, light, erosion, corrosion, and the like. Suitable materials forming a sheath for insulating the working electrical wire lead 130 may include, but are not limited to, rubber, vulcanized rubber, polyvinyl chloride, poly(ether ether ketone), and the like, and any combination thereof.

Because the working electrode 120 is the electrode on which the reaction of interest occurs, as discussed previously, the working electrode 120 is wholly (e.g., in the middle of the transparent sample window 104, as depicted) within the transparent sample window 104. Generally, the working electrode 120 may cover at least about 60% of the area of the transparent sample window 104 through which electromagnetic radiation will pass through. In some embodiments, a portion of the working electrical wire lead 130 may also extend into the transparent sample window 104 through the cell body 102.

In some embodiments, the working electrode 120 may be composed of an electrochemically inert material (including substantially electrochemically inert materials) to serve as a surface on which electrochemical reactions take place. The electrochemically inert material forming the working electrode 120 may include, but is not limited to, an inert metal (e.g., gold, silver, platinum, ruthenium, rhodium, palladium, osmium, iridium, copper, rhenium, mercury, stainless steel, and the like), an inert carbon (e.g., vitreous carbon, pyrolytic carbon, graphite, and the like), a transparent conducting film (e.g., indium tin oxide, fluorine doped tin oxide, doped zinc oxide, and the like), and any combination thereof. In some non-limiting embodiments, platinum may be the inert material for forming the working electrode 120.

Referring now to the counter electrode 122, the counter electrode 132 serves as a conductor to complete the circuit in the cell 100. That is, the counter electrode 122, along with the working electrode 120 provides a circuit over which current is either applied or measured. Generally, the potential of the counter electrode 122 is not measured but is adjusted to balance the reaction occurring on the surface of the working electrode 120. Accordingly, the potential of the working electrode 120 can be measured against the reference electrode 124 without compromising the stability of the reference electrode 124 by passing current over it. Like the working electrode 120, the counter electrode 122 is electrically coupled to the end of a counter electrical wire lead 132. The counter electrical wire lead 132 may be configured identical to the working electrical wire lead 130, or by any means or material discussed with reference to the working electrical wire lead 130, including composition material, insulation, insulation material (i.e., a sheath), electrical wire lead connection, and the like, without departing from the scope of the present disclosure. Accordingly, these configurations will not be discussed again in detail with reference to the counter electrical wire lead 132. It should also be noted that the working electrode 120 and the counter electrode 122 may have electrical wire leads 130 and 132, respectively, that are identical in all respects (e.g., of the same material, insulated identically, and the like), in only some respects (e.g., of the same material, but insulated differently, or vice versa, and the like), or in no respects (e.g., of different material, and insulated differently, and the like), as described above, without departing from the scope of the present disclosure.

Also similar to the working electrode 120, the counter electrode 122 may be composed of any of the electrochemically inert materials discussed above with reference to the working electrode 120. In some embodiments, the working electrode 120 and the counter electrode 122 may of identical material or different material, without departing from the scope of the present disclosure. Likewise, the type of counter electrode 122 may be any type discussed with reference to the working electrode 120 (e.g., a disk electrode, a rotating disk electrode, a rotating ring-disk electrode, etc. as previously discussed). In some embodiments, the working electrode 120 and the counter electrode 122 may be of the same type of a different type, without departing from the scope of the present disclosure.

Referring now to the reference electrode 124, the reference electrode 124 has a stable and known electrical potential. The reference electrode 124 may be used to measure the working electrode potential. The reference electrode 124, like the working electrode 120 and counter electrode 122, is electrically coupled to a reference electrical wire lead 134 that may be configured and made identical to one or both of the working electrical wire lead 130 or the counter electrical wire lead 132, or by any means or material discussed with reference to the working electrical wire lead 130 and counter electrical wire lead 132, including composition material, insulation, insulation material (i.e., a sheath), electrical wire lead connection, and the like, without departing from the scope of the present disclosure. Accordingly, these configurations will not be discussed again in detail with reference to the reference electrical wire lead 134. It should also be noted that the working electrode 120, the counter electrode 122, and the reference counter electrode may have electrical wire leads 130, 132, and 134, respectively, that are identical in all respects (e.g., of the same material, insulated identically, and the like), in only some respects (e.g., of the same material, but insulated differently, or vice versa, and the like), or in no respects (e.g., of different material, and insulated differently, and the like), as described above, without departing from the scope of the present disclosure.

Because the reference electrode 124 should maintain a stable and known electrical potential, they may be made of materials that combat against drift in the electrical potential. Such electrical potential drift may result in quantitative and/or qualitative errors in data collection related to the fluid species being analyzed in the cell 100. The reference electrode 124, accordingly, of the present disclosure may be an electrode including, but not limited to, an aqueous reference electrode (e.g., a standard hydrogen electrode, a normal hydrogen electrode, a reversible hydrogen electrode, a saturated calomel electrode, a copper-copper(II) sulfate electrode, a silver chloride electrode, a pH electrode, a palladium-hydrogen electrode, a dynamic hydrogen electrode, and the like), a non-aqueous reference electrode (e.g., a silver-silver chloride electrode, a quasi-reference electrode, a silver-silver nitrate electrode), or a pseudo-reference electrode (e.g., a silver-silver ion pseudo-reference electrode), or a platinum wire, and the like. The shape of the reference electrode 124 may be any shape suitable for forming the suitable reference electrodes discussed herein, including wire shape, disk shaped, mesh shaped, and the like, without departing from the scope of the present disclosure.

The cell body 102 may include a fluid mixer 160. The fluid mixer may be located in the cell body to recirculate fluid placed therein, as discussed in more detail below. In some embodiments, the fluid mixer may be used to recirculate the fluid in the cell body 102 and the transparent sample window 104 such that fresh transparent sample window fluid enters into the transparent sample window 104 for further testing an analysis. In such a way, multiple tests may be run on a variety of fresh fluid samples in the transparent sample window 104 on a single fluid combination without having to remove any fluid from cell 100. As depicted, the fluid mixer 160 is a mechanical mixer located in the cell body 102; however, any mixer capable circulating the fluid in the cell body 102 and transparent sample window 104 may be used in accordance with the embodiments herein. In some embodiments, the fluid mixer may include, but not be limited to, a mechanical mixer, a magnetic mixer, a sonic mixer, and the like, and any combination thereof.

Although the fluid mixer 160 in FIG. 1 is located at the bottom of the cell body 102 and toward an edge of the cell body 102, the fluid mixer 160 may be present at any location in the cell body 102 provided that the fluid mixer 160 is able to circulate the fluid in the cell body 102 and the transparent sample window 104 in order to refresh the fluid in the transparent sample window 104. Moreover, although a single fluid mixer 160 is shown in FIG. 1, more than one fluid mixer 160, as well as more than one type of fluid mixer 160, may be included in the cell body 102, such as two, three, four, five, or even more. The inclusion of multiple fluid mixers 160 may be beneficial in instances with the volume of the cell body 102 is large and circulation of the fluid therein is more difficult as compared to a smaller volume cell body 102.

The cell body 102 may comprise a plurality of inlets (150, 152, 154, 156, and 158) for introducing fluids into the cell body 102 and the transparent sample window 104. Each inlet, discussed separately below, may extend through the cell body 102 for introducing fluids therethrough. The inlets are each hermetically sealed with reference to the cell body 102 by any means discussed above with reference to the electrodes and electrical wire leads. The inlets may also be formed as tubulars (e.g., flexible or inflexible tubulars) that receive fluids directly from a source, which may be at a downhole location or affixed to a downhole tool such that formation fluid, for example, is directly input into the cell body 102 from the downhole tool. Where the inlets are connected to a tubular or another equipment piece for introducing fluids therethrough, the entirety of the inlet and any associated connections is preferably hermetically sealed or sealable to ensure an airtight configuration of the cell body 102.

As depicted in FIG. 1, the fluid inlets are located on a top portion of the cell body 102. However, they may extend through the cell body 102 at any location (e.g., sides or bottom of the cell body 102) provided that they are able to introduce a volume of fluid into the cell body 102 and the transparent sample window 104, without departing from the scope of the present disclosure. For example, the fluid inlets may have a backstop valve capable of allowing the fluid inlets to introduce fluid into the cell body 102 and transparent sample window 104 even when the fluid inlet is located below a filled volume of the cell body 102.

Similar to the fluid inlets for introducing fluids into the cell body 102 and the transparent sample window 104, the cell body may comprise one or more (one shown) fluid outlet(s) 170 extending through the cell body 102 for removing the fluids from the cell body 102 and transparent sample window 104. The fluid outlet 170 is hermetically sealed with reference to the cell body 102 by any means discussed above with reference to the electrodes and electrical wire leads. The fluid outlet 170 may be located at any location (e.g., top, side, bottom) of the cell body 102, although depicted on the side of the cell body 102 in FIG. 1, without departing from the scope of the present disclosure. Fluid may be removed from the cell 100 through the fluid outlet 170 by any means including, but not limited to, gravity, suction (e.g., pulling a vacuum), and the like, and any combination thereof. In some embodiments, the fluid outlet 170 may be formed as tubulars (e.g., flexible or inflexible tubulars) that allow fluids to be removed therein from the cell 100. Such tubulars may be connected to a source that aids in the removal of the fluid, such as a suction device (e.g., vacuum). Where the inlets are connected to a tubular or another device for removing fluids therethrough, the entirety of the fluid outlet 170 and any associated connections is preferably hermetically sealed or sealable to ensure an airtight configuration of the cell body 102.

Referring back to the fluid inlets in FIG. 1, as depicted, the cell 100 may include a sample inlet 150 through which a sample to be tested is initially introduced into the cell body 102. In some embodiments, when the cell 100 is used in a downhole environment, the sample introduced through the sample inlet 150 may be formation fluid, fluid otherwise introduced into the formation, or a combination thereof. Other sample fluids may also be tested using the cell 100 of the present disclosure to identify the presence or absence of a particular species in the sample fluid.

A solvent inlet 152 may extend through the cell body 102 through which an electrolytic solvent may be included into the cell body 102. The solvent, in conjunction with a supporting electrolyte, which may be introduced through an electrolyte inlet 154, to facilitate electrochemical reactions in the transparent sample window 104 upon applying a voltage potential therethrough. The use of a dual solvent and supporting electrolyte fluid in the cell 100 may facilitate adjustments to be made, such as adjustments to the amount of electrolyte included, which may be step-wise increased during analysis of one or more sample fluids, for example. As used herein, the term "supporting electrolyte" (or simply "electrolyte" herein) refers an electrolyte solution, whose constituents are not electroactive in the range of applied potentials being studied, and whose ionic strength (and, therefore, contribution to the conductivity) is usually much larger than the concentration of an electroactive substance to be dissolved in it.

Suitable solvents for use in the cell 100 may include, but are not limited to, polar solvents, non-polar solvents, and any combination thereof. Specific examples of suitable solvents for use in the cell 100 of the present disclosure may include, but are not limited to, hexane, benzene, toluene, diethyl ether, chloroform, 1,4-dioxane, ethyl acetate, tetrahydrofuran, dichloromethane, acetone, acetonitrile, dimethylformamide, dimethyl sulfoxide, acetic acid, n-butanol, t-butyl alcohol, isopropanol, n-propanol, ethanol, methanol, formic acid, water, carbon tetrachloride, chlorobenzene, cyclohexane, 1,2-dichloroethane, butyl lactate, dipropylene glycol methyl ether, dipropylene glycol dimethyl ether, dimethyl formamide, diethyleneglycol methyl ether, ethyleneglycol butyl ether, diethyleneglycol butyl ether, propylene carbonate, methanol, butyl alcohol, d'limonene, fatty acid methyl esters, and butylglycidyl ether, 1,2,-dimethoxyethane, heptane, glycerin, hexamethylphosphoramide, hexamethylphosphorous triamide, methyl t-butyl ether, methylene chloride, n-methyl-2-pyrrolidinone, nitromethane, pentane, petroleum ether, triethyl amine, tetrahydrofuran, pyridine, o-xylene, m-xylene, p-xylene, octanoic acid, propionic acid, and the like, and any combination thereof.

Suitable supporting electrolytes should remain electroinactive in the voltage potential region of interest. Suitable supporting electrolytes may include any meeting the definition provided above including, but not limited to, any ionic species including, but not limited to, lithium chloride, anhydrous lithium chloride, potassium chloride, perchloric acid, sulfuric acid, hydrochloric acid, sodium hydroxide, potassium hydroxide, chloride, hydroxide, citrate, tartrate, oxylate, potassium cyanide, potassium thiocyanate, ethylenediminetetraacetic acid (EDTA), lithium perchlorate, sodium perchlorate, a tetra-alkyl ammonium salt, tetra-ethyl ammonium salt, tetra-n-butyl ammonium salt, a perchlorate ion, and the like, and any combination thereof. The choice of supporting electrolyte may depend on a number of factors including, but not limited to, the type of solvent selected (e.g., an acidic or alkaline solvent), the voltage potential of interest, the downhole environment in which analysis is being conducted, and the like.

In some embodiments, the supporting electrolyte may be included in the cell body 102 through the electrolyte inlet 154 such that the molar concentration of the supporting electrolyte in the solvent has a molar concentration that is in the range of a lower limit of about $10^{-4}$ moles per liter (mol/L), 0.01 mol/L, 0.05 mol/L, 0.1 mol/L, 0.15 mol/L, 0.2 mol/L, 0.25 mol/L, 0.3 mol/L, 0.35 mol/L, 0.4 mol/L, 0.45 mol/L, and 0.5 mol/L to an upper limit of about 1 mol/L, 0.95 mol/L, 0.9 mol/L, 0.85 mol/L, 0.8 mol/L, 0.75 mol/L, 0.7 mol/L, 0.65 mol/L, 0.6 mol/L, 0.55 mol/L, and 0.5 mol/L, encompassing any value and subset therebetween.

In lieu of the solvent and supporting electrolyte, an ionic fluid may be used for the same purposes in the cell 100. The ionic fluid, in some instances, may be more environmentally friendly than the separate solvent and electrolyte combinations used in the embodiments described herein. The ionic fluid may be introduced into the cell body 102 through the ionic fluid inlet 156. As used herein, the term "ionic fluid" refers to a salt in the liquid state.

Suitable ionic fluids may include, but are not limited to, sodium chloride, lithium chloride, sodium nitrate, aluminum chloride, 1-butyl-3-methylimidazolium hexafluorophosphate ([BMIM]PF6), and any combination thereof.

As used herein, the term "conductive fluid" may be used collectively to refer to both the combination of solvent and supporting electrolyte and the ionic fluid that may be used in accordance with the present disclosure.

A detection species may be included in the cell body 102 through a detection species inlet 158. The detection species may react with a species in the sample fluid (e.g., formation fluid or downhole fluid), causing a conformational (e.g., isomers), colorimetric, or other change that can be detected by spectroelectrochemistry means, as described in detail below. In some embodiments, rather than introducing the detection species into the cell body 102 through the detection species inlet 150 for entrance into the transparent sample window 104 and detection, the detection species may be partially (i.e., partially or wholly) coated onto the working electrode 120 in the transparent sample window 104, onto the transparent sample window 104 itself, or any combination thereof. For example, in some embodiments, the transparent sample window 104 may be made of aluminum oxide and the detection species may be surface treated with titanium oxide or another material (e.g., anodizing) that attaches to a functional group on the detection species. In other embodiments, the transparent sample window 104 may be etched into a honeycomb shape wherein layers of the detection species may be coated thereon to allow for wear. Any other type of coating, such as functionalization (e.g., using nano-gold particles), may be used in accordance with the methods described herein. In such embodiments where the transparent sample window 104 is at least partially coated with one or more detection species, any portion of the transparent sample window 104 may be coated, such as a single side, multiple sides, and the like, provided that it is in the optical path. Moreover, different types of detection species may be coated thereon.

In other embodiments, the detection species may be coated onto an optically inert film (which may be made of any material used to form the transparent sample window 104) placed in transparent sample window 104. In such instances, a type of "film strip" system may be used such that the film is moved (e.g., like on a film cartridge device) when the detection species is exhausted or moved when a different type of detection species is desired. In other embodiments, the detection species may be free floating in the cell body 102 and/or the transparent sample window 104.

In some embodiments, the detection species may include, but not be limited to, a porphyrin, a metalloporphyrin comprising a metal ion, a metalloporphyrin-protein complex, and any combination thereof. The detection species may be included in the cell body 102 in any amount able to electrochemically react with a sample of interest in the transparent sample window 104 of the cell 100. In some embodiments, the detection species may be included in the cell body 102 with the conductive fluid (e.g., the combination solvent and supporting electrolyte or the ionic fluid) in an amount in the range of from a lower limit of about $10^{-4}$ mol/cm$^3$, 0.1 mol/cm$^3$, 0.5 mol/cm$^3$, 1.5 mol/cm$^3$, 2 mol/cm$^3$, 2.5 mol/cm$^3$, 3 mol/cm$^3$, 3.5 mol/cm$^3$, 4 mol/cm$^3$, 4.5 mol/cm$^3$, and 5 mol/cm$^3$ to an upper limit of about 10 mol/cm$^3$, 9.5 mol/cm$^3$, 9 mol/cm$^3$, 8.5 mol/cm$^3$, 8 mol/cm$^3$, 7.5 mol/cm$^3$, 7 mol/cm$^3$, 6.5 mol/cm$^3$, 6 mol/cm$^3$, 5.5 mol/cm$^3$, and 5 mol/cm$^3$, encompassing any value and subset therebetween. Examples of the function of some of the detection species disclosed herein are provided below.

Porphyrins are a group of heterocyclic macrocycle organic compounds composed of four modified pyrrole subunits interconnected at their alpha-carbon atoms via methane (=CH—) bridges. Porphyrins possess, among other things, excellent electro-optical properties and fluorescence alteration (or switching). Suitable porphyrins for use in the present disclosure may include, but are not limited to, a porphine, pyropheophorbide-a, pheophorbide, chlorin e6, purpurin, purpurinimide, octatethylporphyrin, tetrakis(o-aminophenyl)porphyrin, meso-tetraphenylporphyrin, tetra phenyl porphyrin, tetra fluoro chloro phenyl porphyrin, tetra dichloro phenyl porphyrin, and the like, and any combination thereof.

Metalloporphyrins are formed by the combination of a porphyrin with a metal ion. Any porphyrin capable of chemically interacting (e.g., binding) with a metal ion may be used in accordance with the present disclosure, including each of the porphyrins previously mentioned. Suitable metal ions in forming the metalloporphyrins may include, but are not limited to, iron(II), iron(III), chromium(II), chromium (III), cobalt(II), cobalt(III), copper(II), lead(II), lead(IV), mercury(I), mercury(II), tin(II), tin(IV), cadmium, zinc, gold(III), manganese(II), manganese(III), manganese(IV), aluminum, nickel(II), nickel(III), antimony(III), antimony (V), vanadium, and the like, and any combination thereof. Specific examples of metalloporphyrins may include, but are not limited to, heme, and the like, and any combination thereof.

In some embodiments, the detection species may be a metalloporphyrin-protein complex. Suitable metalloporphyrin-protein complexes for use in the present disclosure may include, but are not limited to, hemoglobin, myoglobin, cytochrome, catalase, endothelial nitric oxide synthase, methemoglobin, chlorophyll, isomers thereof, and any combination thereof.

Figure 2:
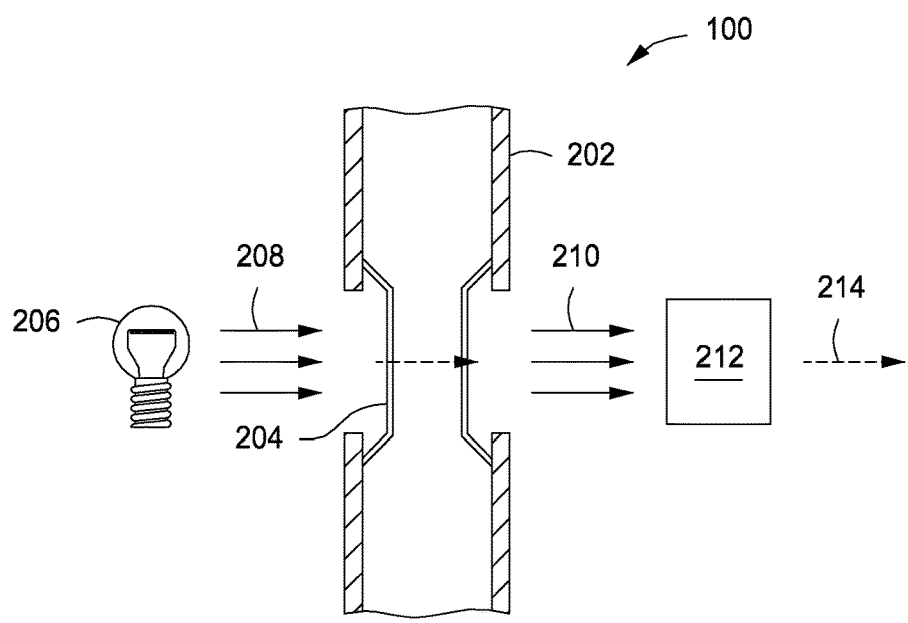
FIG. 2 depicts a block diagram non-mechanistically illustrating how spectroelectrochemical evaluation of a sample is achieved using the thin-layer spectroelectrochemical cell according to one or more embodiments of the present disclosure.

Referring now to FIG. 2, with continued reference to FIG. 1, illustrated is a block diagram non-mechanistically illustrating how spectroelectrochemical evaluation of a sample is achieved using the thin-layer spectroelectrochemical cell according to one or more embodiments of the present disclosure. A thin-layer spectroelectrochemical cell 200 ("cell 200") may be substantially similar to the cell 100 of FIG. 1. As shown, the cell 200 has a cell body 202 and a transparent sample window 204. Through the fluid inlets (FIG. 1), a conductive fluid, a detection species, and a sample of interest may be introduced into the cell body 202, wherein a portion of the conductive fluid, the detection species, and the sample of interest enter into the transparent sample window 204. This may be achieved by filling the various fluids above the transparent sample window 204 or by mixing using the fluid mixer 160 (FIG. 1), or other means, such as natural or manmade (e.g., as a result of a formation operation) vibrations in a downhole environment. The combination of conductive fluid, the detection species, and the sample in the transparent sample window 204 is referred to herein as "transparent sample window fluid." The transparent sample window fluid is the fluid whose spectra and electrochemical behavior is evaluated to determine a characteristic of the sample of interest.

First, a voltage potential may be applied across the transparent sample window 204 using the potentiostat 140 (FIG. 1) connected to the electrical wire leads of the working electrode 120 (FIG. 1), counter electrode 122 (FIG. 1), and the reference electrode 124 (FIG. 1). The applied voltage potential drives an electrochemical reaction between the detection species and the sample in the transparent sample window fluid. The spectra of that electrochemical reaction is collected as described below and indicative of a characteristic of the sample due to the oxidized or reduced spectra of the detection species based on binding or otherwise associating with the sample. The voltage potential may be applied continuously or in a stepwise fashion where the voltage is increased throughout the duration of testing.

An electromagnetic radiation source 206 emits electromagnetic radiation into the optical path defined by the transparent sample window 204 (i.e., through the transparent sample window 204). The electromagnetic radiation source 206 may be, but is not limited to, single-wavelength source, a multi-wavelength source, a full spectrum wavelength source, and any combination thereof. Specific examples of suitable electromagnetic radiation sources 206 may include, but are not limited to, a light bulb, a light emitting device, a laser, a blackbody, a photonic crystal, and any combination thereof. The electromagnetic radiation source produces electromagnetic radiation 208 which may be in the non-limiting form of infrared radiation, near-infrared radiation, visible light, ultraviolet light, and any combination thereof.

The electromagnetic radiation 208 is emitted from the electromagnetic radiation source and optically interacts with the transparent sample window fluid to generate modified electromagnetic radiation 210. As used herein, the term "optically interact," or variations thereof, refers to reflection, transmission, absorption, fluorescence, scattering, or diffraction of electromagnetic radiation. In some embodiments, the electromagnetic radiation 208 may be optically interacted with the transparent sample window fluid through the transparent sample window 204 without a voltage potential being applied thereto, reflecting the spectra of the transparent sample window fluid without its electrochemical behavior (e.g., in a non-reduced and/or non-oxidized state). In other embodiments, the electromagnetic radiation 208 may be optically interacted with the transparent sample window fluid through the transparent sample window 204 with a voltage potential being applied thereto, reflecting the spectra and electrochemical (e.g., in a reduced and/or oxidized state) of the transparent sample window fluid.

The modified electromagnetic radiation 210 may be received by a detector 212 that generates an output signal 214 corresponding to a characteristic of the sample of interest (e.g., formation fluid or downhole fluid). The detector 212 may be any device capable of detecting electromagnetic radiation, and may generally be characterized as a photodetector, which, as used herein, includes spectrometers, photometers, integrated computational elements coupled with a photodetector, and the like. In some instances, the detector 212 may be capable of detecting the intensity of electromagnetic radiation as a function of wavelength. Specific photodetectors that may be used as or within the detector 212 in the embodiments described herein may include, but are not limited to, a silicon photodetector, an InGaAs photodetector, a photomultiplier tube, and the like, and any combination thereof.

The optical path defined by the transparent sample window 204 may be a length from the electromagnetic radiation source 206 to the detector 210. In some embodiments, the electromagnetic radiation 208 is directly emitted into the optical path while, in other embodiments, the electromagnetic radiation 208 may be reflected from another surface (e.g., mirror or lens) and directed into the optical path for optical interaction with the transparent sample window fluid in the transparent sample window 204. In some embodiments, the optical path between the electromagnetic radiation source and the detector has a length in the range of a lower limit of about 1 mm, 1.5 mm, 2 mm, 2.5 mm, 3 mm, 3.5 mm, 4 mm, 4.5 mm, and 5 mm to an upper limit of about 10 mm, 9.5 mm, 9 mm, 8.5 mm, 8 mm, 7.5 mm, 7 mm, 6.5 mm, 6 mm, 5.5 mm, and 5 mm, encompassing any value and subset therebetween.

As shown, the detector 212 opposite the electromagnetic radiation source 206. However, in some embodiments, one side of the transparent sample window 204 may be a reflective surface and the detector 212 may be located on the same side of the transparent sample window 204 as the electromagnetic radiation source 206, wherein the emitted electromagnetic radiation 208 transmits through the transparent sample window 204, optically interacts with the fluid therein, reflects off the reflective surface back through the side of the transparent sample window 204 to a detector 212. In such a configuration, only one side of the transparent sample window 204 is transparent. In other embodiments, there may be a single transparent sample window 204 where light interaction with the fluid therein occurs through attenuated total internal reflection.

In some embodiments, the thin-layer spectroelectrochemical cell, the potentiostat, the electromagnetic radiation source, and the detector may form a single, enclosed device that may be transported and operated as a single unit. In other embodiments, the thin-layer spectroelectrochemical cell, the potentiostat, the electromagnetic radiation source, and the detector may form separate components to perform the methods described herein. Whether as a single device or as separate components, in some embodiments, the thin-layer spectroelectrochemical cell, the potentiostat, the electromagnetic radiation source, and the detector may be located at a downhole location in a wellbore in a subterranean formation. They may be similarly located in a wellbore during or as part of a subterranean formation operation, or on a downhole tool during performance of a subterranean formation operation such as, for example, a measurement-while-drilling tool, a drill string, a formation tester, a wireline, a drill stem test tool, and any combination thereof. Inclusion of the thin-layer spectroelectrochemical cell, the potentiostat, the electromagnetic radiation source, and the detector as part of these tools may facilitate collection of formation fluid for use as the sample in the methods described herein, such as if the thin-layer spectroelectrochemical cell is integral to a formation tester that is designed to collect formation fluid. In yet other embodiments, the thin-layer spectroelectrochemical cell, the potentiostat, the electromagnetic radiation source, and the detector may be located in a pipeline, such as a pipeline comprising a hydrocarbon fluid.

Referring again to FIG. 2, the detector 210 may generate an output signal 214 corresponding to a characteristic of the sample of interest. In some embodiments, the output signal may include, but is not limited to, a voltammetry signal (e.g., cyclic voltammetry, linear sweep voltammetry, staircase voltammetry, squarewave voltammetry, anodic stripping voltammetry, differential pulse voltammetry), an electromagnetic radiation absorption spectroscopy signal, and any combination thereof.

In some embodiments, the output signal 214 may be graphically displayed (e.g., as a voltammogram, a spectrogram, a data chart, and the like, and combinations thereof). For example, the output signal 214 may be conveyed to or otherwise received by a signal processor (not shown) communicably coupled the detector 214. The signal processor may be a computer including a non-transitory machine-readable medium configured to graphically display the output signal 214, corresponding to a characteristic of the sample of interest.

Computer hardware used to graphically display the output signal 214 described herein may include a processor configured to execute one or more sequences of instructions, programming stances, or code stored on a non-transitory, computer-readable medium. The processor may be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware may further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

In some embodiments, the output signal 214 corresponds to the presence and/or the absence of an analyte including, but are not limited to, carbon dioxide, hydrogen sulfide, a mercaptan, carbon monoxide, nitric oxide, mercury, and any combination thereof. The detection of these analytes may be particularly beneficial because many are natural components in hydrocarbon fluids or formation water that are hazardous to flora and fauna. For example, hydrogen sulfide is extremely poisonous, corrosive, flammable, and explosive. Removal of hydrogen sulfide from fluids may be possible, but without knowledge of its existence and/or concentration, its removal becomes much more cumbersome. As another example, injection of produced water back into a subterranean formation (either in production wells or injection wells) having an oxygen content (i.e., oxygen molecules) may severely hinder production of the well due to corrosion, bacterial growth, and the like. However, these analytes are often difficult to detect in the laboratory because transport time to the laboratory typically results in degradation (e.g., absorption). Moreover, the lower the levels of these analytes in a particular formation fluid sample, the more difficult they are to detect.

In some embodiments, the output signal 214 may be used to determine a concentration of one or more analytes in a sample fluid, thereby enabling an operator to glean information regarding the overall analyte content of a particular portion or entire area of a wellbore penetrating a hydrocarbon reservoir or water reservoir. For example, the concentration of a particular analyte may be tied to the time it takes for the detection species spectra to change (e.g., indicating an uptake of the analyte of interest).

Use of the thin-layer spectroelectrochemical cell, the potentiostat, the electromagnetic radiation source, and the detector as used herein permits real-time or substantially real-time identification of the presence or absence of analytes, including concentration, using a detection species, as described above, of a porphyrin, a metalloporphyrin comprising a metal ion, a metalloporphyrin-protein complex, and any combination thereof. These detection species chemically interact (e.g., by bonding) with analytes and respond with conformational, fluorescent, colorimetric, or other detectable changes that can be detected by the detector 212 of the present disclosure. That is, the electrochemical and spectroscopic properties of the bound and unbound species are very different and detectable. Application of a voltage potential across these detection species further results in a change in their optical properties, resulting in an enhanced optical spectra that is more readily detectable, particularly when a low concentration of the analyte is present. In other embodiments, the application of a voltage potential across the detection species changes the electrostatic properties of the detection species and the binding properties therein, which may permit them to more readily bind to a analyte (or a component in a analyte, for example) in a sample fluid, or a specific type of analyte, thereby also increasing the subsequent optical signal and selectivity. Moreover, the change in the binding properties allows the analytes to be unbound by the detection species when the voltage potential is reversed or otherwise changed. In yet other instances, the voltage potential may affect the electrostatic properties of the detection species, including the location of the metal ions in a metalloporphyrin (e.g., whether they are exposed or encompassed in the porphyrin, and the like), for example, which affects the optical spectra. In some embodiments, the resultant output signal 214 can be used to create a voltammogram or a spectrogram related to the presence or absence of a particular VOC.

The porphyrins, metal comprising metalloporphyrins, and the metalloporphyrin-protein complexes are extremely sensitive detection species. For example, they can recover a proportional amount of oxygen from the air that is less than about 20%. For other materials, like the VOC carbon monoxide, they may recover about 2 or 3 parts per million (ppm) out of air. Accordingly, they are able to concentrate certain materials of interest (analytes) and provide a proportional response while it is concentrating them. They are also able to withstand extreme temperature and pressures, such as those found in subterranean formations discussed above.

For example, in some embodiments, the detection species is the metalloporphyrin-protein complex hemoglobin, which may be used to detect carbon dioxide in a sample of interest using the methods described herein. Hemoglobin has more than one shape and can undergo conformational changes in its structure, based on environmental conditions, including the presence of analytes. There are two alternative structures of hemoglobin: the relaxed structure (R), which has a greater oxygen affinity, and the tense structure (T), which has lower affinity for oxygen. The change between the T and R structures is the result of a rotation of 15° between the two alpha-beta dimers. This rotation changes the bonds between the side chains of the alpha-beta dimers in the F helix, causing the heme molecule of the hemoglobin to change positions. In the T structure, the iron ion is pulled out of the plane of the porphyrin ring and becomes less accessible for oxygen to bind to it, thus reducing its affinity to oxygen. In the R structure, the iron atom is in the plane of the porphyrin ring and is accessible for oxygen to bind to it, thus increasing its oxygen affinity. Consequently, the hemoglobin molecule's unique structure enables it to shift between the T and R structures in the presence or absence of oxygen.

However, the oxygen affinity of hemoglobin can also be regulated by external chemical factors, including the analyte carbon dioxide ($CO_2$). In the presence of a sample $CO_2$, the $CO_2$ binds to the N-terminus of the alpha globin molecule of hemoglobin. The $CO_2$ binds more readily to the globin in the T structure, rather than the R structure. The uptake of $CO_2$ by hemoglobin facilitates the release of oxygen by the T structure and a conformational change to the R structure. Hemoglobin bound to $CO_2$ has a distinct visible absorption spectra. Hemoglobin possesses electrochemical behavior in the range of a lower limit of about −2.0 V, −1.75 V, −1.5 V, −1.25 V, −1.0 V, −0.75 V, −0.5 V, −0.25 V, and 0 V to an upper limit of about +2.0 V, +1.75 V, +1.5 V, +1.25 V, +1.0 V, +0.75 V, +0.5 V, +0.25 V, and 0 V, encompassing any value and subset therebetween. The behavior of the reduced or oxidized hemoglobin produces a different binding ability with the $CO_2$, and also produces a distinct absorption spectra that can be evaluated to determine the presence of $CO_2$ with enhanced sensitivity. Application of a voltage potential applied in this example may be in the range discussed above, encompassing any value and subset therebetween As another example, the methods described herein may be used to detect the analyte hydrogen sulfide ($H_2S$). In one embodiment, methemoglobin may be used as the detection species for the analyte $H_2S$. Methemoglobin is a form of the oxygen-carrying metalloporphyrin-protein complex hemoglobin, in which iron(III) rather than iron(II) is the metal ion therein. In the presence of $H_2S$ and oxygen, methemoglobin undergoes an irreversible reaction, forming sulfhemoglobin (SufHb), which is a green compound having a distinct absorption band at 618 nanometers (nm). The green compound can be easily detected using the methods of the present disclosure to determine whether $H_2S$ is present in a sample of interest.

Application of a voltage potential applied in this example may be in the range of a lower limit of about −2.0 V, −1.75 V, −1.5 V, −1.25 V, −1.0 V, −0.75 V, −0.5 V, −0.25 V, and 0 V to an upper limit of about +2.0 V, +1.75 V, +1.5 V, +1.25 V, +1.0 V, +0.75 V, +0.5 V, +0.25 V, and 0 V, encompassing any value and subset therebetween.

The use of an ultraviolet (UV) electromagnetic source, or other means of UV irradiation, in the embodiments herein where $H_2S$ is the analyte of interest may also aid in increasing a stronger infrared signal for detection. The UV irradiation of the $H_2S$ converts it to $SO_2$, which has a stronger infrared absorption.

Another analyte, mercury, may be present in formation fluids, typically in the form of elemental mercury. In some instances, mercury may be present in the range of from 0.1 to 20,000 microgram per kilogram (pg/kg). In some embodiments, the detection species may be a metalloporphyrin comprising copper(II) metal ion, or other metal ion that reacts with mercury. The voltage potential supplied across the transparent sample window of the thin-layer spectroelectrochemical cell may be such that the placement copper (II) metal ion is exposed to the mercury, which is highly reactive with the copper. This reactivity results in denaturing the metalloporphyrin and a detectable optical spectra. In some embodiments, the voltage potential applied in this example may be in the range of a lower limit of about −2.0 volts (V), −1.8 V, −1.6 V, −1.4 V, −1.2 V, −1.0 V, −0.8 V, −0.6 V, −0.4 V, −0.2 V, −0.0 V, +0.2 V, +0.4 V, and +0.6 V to an upper limit of about +3.0 V, +2.8 V, +2.6 V, +2.4 V, +2.2 V, +2.0 V, +1.8 V, +1.6 V, +1.4 V, +1.2 V, +1.0 V, +0.8 V, and +0.6 V, encompassing any value and subset therebetween.

It should also be noted that the various drawings provided herein are not necessarily drawn to scale nor are they, strictly speaking, depicted as optically correct as understood by those skilled in spectroelectrochemistry. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Aspects and examples disclosed herein include:

Embodiment/Example A (Method Example)

A method comprising: providing a spectroelectrochemistry cell, the spectroelectrochemistry cell comprising: a cell body that has a first volume, a transparent sample window defined in the cell body and in fluid communication therewith, the transparent sample window defining an optical path through the cell body and having a second volume, a working electrode extending through the cell body and into the transparent sample window in the optical path, the working electrode electrically coupled to a working electrical wire lead at a first end thereof, a counter electrode extending through the cell body, the counter electrode electrically coupled to a counter electrical wire lead at a first end thereof, a reference electrode extending through the cell body, the reference electrode electrically coupled to a reference electrical wire lead at a first end thereof, and a fluid mixer located within the cell body; electrically coupling a second end of the working electrical wire lead, a second end of the counter electrical wire lead, and a second end of the reference electrical wire lead to a potentiostat; introducing a conductive fluid into the cell body; introducing a detection species into the cell body; introducing a sample into the cell body, wherein a portion of the conductive fluid, the detection species, and the sample enter into the transparent sample window in the optical path, thereby forming transparent sample window fluid; applying a voltage potential with the potentiostat across the transparent sample window to drive an electrochemical reaction between the detection species and the sample in the transparent sample window fluid; transmitting electromagnetic radiation with an electromagnetic radiation source into the optical path through the transparent sample window, thereby optically interacting the electromagnetic radiation with the transparent sample window fluid to generate modified electromagnetic radiation; receiving the modified electromagnetic radiation with a detector; and generating an output signal corresponding to a characteristic of the sample.

Embodiment/Example A may have one or more of the following additional elements in any combination:

Element A1: Wherein the detection species is free-floating.

Element A2: Wherein the detection species is at least partially coated onto a location in the optical path selected from the group consisting of the working electrode, the transparent sample window, and any combination thereof.

Element A3: Wherein the detection species selected from the group consisting of a porphyrin, a metalloporphyrin comprising a metal ion, a metalloporphyrin-protein complex, and any combination thereof.

Element A4: Wherein the detection species is a metalloporphyrin comprising a metal ion, and the metal ion in the metalloporphyrin is selected from the group consisting of iron(II), iron(III), chromium(II), chromium(III), cobalt(II), cobalt(III), copper(II), lead(II), lead(IV), mercury(I), mercury(II), tin(II), tin(IV), cadmium, zinc, gold(III), manganese(II), manganese(III), manganese(IV), aluminum, nickel (II), nickel(III), antimony(III), antimony(V), vanadium, and any combination thereof.

Element A5: Wherein the detection species selected is a metalloporphyrin-protein complex selected from the group consisting of hemoglobin, myoglobin, cytochrome, catalase, endothelial nitric oxide synthase, methemoglobin, chlorophyll, isomers thereof, and any combination thereof.

Element A6: Wherein the conductive fluid is selected from the group consisting of a combination solvent and supporting electrolyte, an ionic fluid, and any combination thereof.

Element A7: Wherein the output signal is selected from the group consisting of a voltammetry signal, an electromagnetic radiation absorption spectroscopy signal, and any combination thereof.

Element A8: Wherein the output signal corresponds to a presence and/or absence of an analyte in the sample.

Element A9: Wherein the output signal corresponds to a presence and/or absence of an analyte in the sample, wherein the analyte is selected from the group consisting of carbon dioxide, hydrogen sulfide, a mercaptan, carbon monoxide, nitric oxide, mercury, and any combination thereof.

Element A10: Further comprising mixing the conductive fluid, the detection species, and the sample in the spectroelectrochemistry cell, thereby replacing the transparent sample window fluid with a fresh transparent sample window fluid.

Element A11: Wherein the sample is formation fluid from a subterranean formation.

Element A12: Wherein the spectroelectrochemistry cell, the potentiostat, the electromagnetic radiation source, and the detector are located in a wellbore in a subterranean formation.

Element A13: Wherein the spectroelectrochemistry cell, the potentiostat, the electromagnetic radiation source, and the detector are located in a wellbore in a subterranean formation on a tool selected from the group consisting of a measurement-while-drilling wireline, a drill string, a formation tester, a wireline, a drill stem test tool, and any combination thereof.

Element A14: Wherein the spectroelectrochemistry cell, the potentiostat, the electromagnetic radiation source, and the detector are located in a wellbore in a subterranean formation, and wherein the sample is formation fluid from the wellbore in the subterranean formation.

Element A15: Wherein the spectroelectrochemistry cell, the potentiostat, the electromagnetic radiation source, and the detector are located in a pipeline comprising hydrocarbon fluid.

By way of non-limiting example, exemplary combinations applicable to A include: A with A1, A3, and A6; A with A6, A9, and A15; A with A2, A5, A8, and A11; A with A1, A2, A3, and A15; A with A12, A13, and A14; A with A4, A7, and A15; A with A10 and A11; A with A3, A9, and A12.

Embodiment/Example B (System Example)

A system comprising: a spectroelectrochemistry cell comprising: a cell body that has a first volume, a transparent sample window defined in the cell body and in fluid communication therewith, the transparent sample window defining an optical path through the cell body and having a second volume, a working electrode extending through the cell body and into the transparent sample window in the optical path, the working electrode electrically coupled to a working electrical wire lead at a first end thereof, a counter electrode extending through the cell body, the counter electrode electrically coupled to a counter electrical wire lead at a first end thereof, a reference electrode extending through the cell body, the reference electrode electrically coupled to a reference electrical wire lead at a first end thereof, and a fluid mixer located within the cell body; a potentiostat electrically coupled to a second end of the working electrical wire lead, a second end of the counter electrical wire lead, and a second end of the reference electrical wire lead, wherein the potentiostat applies a voltage potential across the transparent sample window; an electromagnetic radiation source that emits electromagnetic radiation into the optical path through the transparent sample window, wherein the electromagnetic radiation optically interacts with a transparent sample window fluid to generate modified electromagnetic radiation; and a detector that receives the modified electromagnetic radiation.

Embodiment/Example B may have one or more of the following additional elements in any combination:

Element B1: Wherein the spectroelectrochemistry cell, the potentiostat, the electromagnetic radiation source, and the detector are located in a wellbore in a subterranean formation.

Element B2: Wherein the spectroelectrochemistry cell, the potentiostat, the electromagnetic radiation source, and the detector are located in a wellbore in a subterranean formation on a tool selected from the group consisting of a measurement-while-drilling wireline, a drill string, a formation tester, a wireline, a drill stem test tool, and any combination thereof.

Element B3: Wherein the spectroelectrochemistry cell, the potentiostat, the electromagnetic radiation source, and the detector are located in a pipeline comprising hydrocarbon fluid.

By way of non-limiting example, exemplary combinations applicable to B include: B with B1 and B2; B with B1 and B3; B with B2 and B3; B with B1, B2, and B3.

Embodiment/Example C (Cell Example)

A spectroelectrochemical cell comprising: a cell body that has a first volume; a transparent sample window defined in the cell body and in fluid communication therewith, the transparent sample window defining an optical path through the cell body and having a second volume; a working electrode extending through the cell body and into the transparent sample window in the optical path, the working electrode electrically coupled to a working electrical wire lead at a first end thereof; a counter electrode extending through the cell body, the counter electrode electrically coupled to a counter electrical wire lead at a first end thereof; a reference electrode extending through the cell body; the reference electrode electrically coupled to a reference electrical wire lead at a first end thereof; a sample inlet extending through the cell body; a solvent inlet extending through the cell body; an electrolyte inlet extending through the cell body; an ionic fluid inlet extending through the cell body; a detection species inlet extending through the cell body, a fluid outlet extending through the cell body; and a fluid mixer located within the cell body.

Embodiment/Example C may have one or more of the following additional elements in any combination:

Element C1: Wherein a second end of the working electrical wire lead, a second end of the counter electrical wire lead, and a second end of the reference electrical wire lead are each electrically coupled to a potentiostat.

Element C2: Wherein the cell body is composed of a material selected from the group consisting of poly(ether ketone), poly(ether ether ketone), poly(ether ketone ketone), poly(ether ether ketone ketone), poly(ether ketone ether ketone ketone), poly(methyl methacrylate), polyethylene, polypropylene, polystyrene, polyvinyl chloride, polytetrafluoroethylene, polycarbonate, polybenzimidazole, a corrosion resistant metal, a metal alloy, a superalloy, and any combination thereof.

Element C3: Wherein the transparent sample window is composed of a material selected from the group consisting of glass, quartz, sapphire, fused quartz, aluminum oxide, and any combination thereof.

Element C4: Wherein the fluid mixer is selected from the group consisting of a magnetic mixer, a sonic mixer, a mechanical mixer, and any combination thereof.

Element C5: Wherein the first volume of the cell body is in the range of about 0.02 ml to about 5000 ml.

Element C6: Wherein the second volume of the transparent sample window is in the range of about 0.01 ml to about 1.0 ml.

Element C7: Wherein the working electrode and the counter electrode are each composed of an identical or different electrochemically inert material.

Element C8: Wherein the working electrode and the counter electrode are each composed of an identical or different electrochemically inert material, and wherein the electrochemically inert material is selected from the group consisting of an inert metal, an inert carbon, a transparent conducting film, and any combination thereof.

Element C9: Wherein the working electrode is at least partially coated with a detection species.

Element C10: Wherein the reference electrode is an aqueous reference electrode, a non-aqueous reference electrode, a pseudo-reference electrode, or a platinum wire electrode.

Element C11: Wherein an electrode selected from the group consisting of the working electrode, the counter electrode, the reference electrode and any combination thereof is at least partially coated with a functional coating of nano-gold particles.

By way of non-limiting example, exemplary combinations applicable to C include: C with C1 and C3; C with C4, C5, and C11; C with C1 and C2; C with C2, C6, and C10; C with C1, C2, C3, C4, C5, C6, C7, C8, C9, C10, and C11; C with C8 and C11; C with C4, C5, and C8; C with C3, C6, C8, and C11.

Embodiment/Example D (Apparatus Example)

An apparatus comprising: a spectroelectrochemical cell including: a cell body that has a first volume, a transparent sample window defined in the cell body and in fluid communication therewith, the transparent sample window defining an optical path through the cell body and having a second volume, a working electrode extending through the cell body and into the transparent sample window in the optical path, the working electrode electrically coupled to a working electrical wire lead at a first end thereof, a counter electrode extending through the cell body, the counter electrode electrically coupled to a counter electrical wire lead at a first end thereof, a reference electrode extending through the cell body, the reference electrode electrically coupled to a reference electrical wire lead at a first end thereof, a sample inlet extending through the cell body, a solvent inlet extending through the cell body, an electrolyte inlet extending through the cell body, an ionic fluid inlet extending through the cell body, a detection species inlet extending through the cell body, a fluid outlet extending through the cell body, and a fluid mixer located within the cell body; an electromagnetic radiation source that emits electromagnetic radiation into the optical path through the transparent window, wherein the electromagnetic radiation optically interacts with a transparent window sample to generate modified electromagnetic radiation; and a detector that receives the modified electromagnetic radiation to generate an output signal, the output signal corresponding to a characteristic of the sample.

Embodiment/Example D may have one or more of the following additional elements in any combination:

Element D1: Wherein a second end of the working electrical wire lead, a second end of the counter electrical wire lead, and a second end of the reference electrical wire lead are each electrically coupled to a potentiostat.

Element D2: Wherein the cell body is composed of a material selected from the group consisting of poly(ether ketone), poly(ether ether ketone), poly(ether ketone ketone), poly(ether ether ketone ketone), poly(ether ketone ether ketone ketone), poly(methyl methacrylate), polyethylene, polypropylene, polystyrene, polyvinyl chloride, polytetrafluoroethylene, polycarbonate, polybenzimidazole, a corrosion resistant metal, a metal alloy, a superalloy, and any combination thereof.

Element D3: Wherein the transparent sample window is composed of a material selected from the group consisting of glass, quartz, sapphire, fused quartz, aluminum oxide, and any combination thereof.

Element D4: Wherein the fluid mixer is selected from the group consisting of a magnetic mixer, a sonic mixer, a mechanical mixer, and any combination thereof.

Element D5: Wherein the first volume of the cell body is in the range of about 0.02 ml to about 5000 ml.

Element D6: Wherein the second volume of the transparent sample window is in the range of about 0.01 ml to about 1.0 ml.

Element D7: Wherein the working electrode and the counter electrode are each composed of an identical or different electrochemically inert material.

Element D8: Wherein the working electrode and the counter electrode are each composed of an identical or different electrochemically inert material, and wherein the electrochemically inert material is selected from the group consisting of an inert metal, an inert carbon, a transparent conducting film, and any combination thereof.

Element D9: Wherein the working electrode is at least partially coated with a detection species.

Element D10: Wherein the reference electrode is an aqueous reference electrode, a non-aqueous reference electrode, a pseudo-reference electrode, or a platinum wire electrode.

Element D11: Wherein an electrode selected from the group consisting of the working electrode, the counter electrode, the reference electrode and any combination thereof is at least partially coated with a functional coating of nano-gold particles.

Element D12: Wherein the electromagnetic radiation source is a single-wavelength source, a multi-wavelength source, a full spectrum wavelength source, and any combination thereof.

Element D13: Wherein the electromagnetic radiation source is selected from the group consisting of a light bulb, a light emitting device, a laser, a blackbody, a photonic crystal, and any combination thereof.

Element D14: Wherein the electromagnetic radiation is selected from the group consisting of infrared radiation, near-infrared radiation, visible light, ultraviolet light, and any combination thereof.

Element D15: Wherein the optical path between the electromagnetic radiation source and the detector is a length in the range of about 1 mm to about 10 mm.

Element D16: Wherein the detector is a photodetector.

Element D17: Wherein the output signal is selected from the group consisting of a voltammetry signal, an electromagnetic radiation absorption spectroscopy signal, and any combination thereof.

Element D18: Wherein the output signal is graphically displayed.

By way of non-limiting example, exemplary combinations applicable to D include: D with D1, D4, and D18; D with D2, D3, D7, and D17; D with D1, D2, D3, D4, D5, D6, D7, D8, D9, D10, D11, D12, D13, D14, D15, D16, D17, and D18; D with D5, D7, and D10; D with D10, D11, D13, and D16; D with D15 and D18; D with D1, D8, and D12.

Therefore, the embodiments disclosed herein are well adapted to attain the ends and advantages mentioned as well as those that are inherent therein. The particular embodiments disclosed above are illustrative only, as they may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
   providing a spectroelectrochemistry cell,
   the spectroelectrochemistry cell comprising:
   a cell body that has a first volume,
   a transparent sample window defined in the cell body and in fluid communication therewith, the transparent sample window defining an optical path through the cell body and having a second volume,
   a working electrode extending through the cell body and into the transparent sample window in the optical path, the working electrode electrically coupled to a working electrical wire lead at a first end thereof, a counter electrode extending through the cell body, the counter electrode electrically coupled to a counter electrical wire lead at a first end thereof,
   a reference electrode extending through the cell body, the reference electrode electrically coupled to a reference electrical wire lead at a first end thereof, and
   a fluid mixer located within the cell body;
   electrically coupling a second end of the working electrical wire lead, a second end of the counter electrical wire lead, and a second end of the reference electrical wire lead to a potentiostat;
   introducing a conductive fluid into the cell body;
   introducing a detection species into the cell body;
   introducing a sample into the cell body, wherein a portion of the conductive fluid, the detection species, and the sample enter into the transparent sample window in the optical path, thereby forming transparent sample window fluid;
   applying a voltage potential with the potentiostat across the transparent sample window to drive an electrochemical reaction between the detection species and the sample in the transparent sample window fluid;
   transmitting electromagnetic radiation with an electromagnetic radiation source into the optical path through the transparent sample window, thereby optically interacting the electromagnetic radiation with the transparent sample window fluid to generate modified electromagnetic radiation;
   receiving the modified electromagnetic radiation with a detector; and
   generating an output signal corresponding to a characteristic of the sample.

2. The method of claim 1, wherein the detection species is free-floating.

3. The method of claim 1, wherein the detection species is at least partially coated onto a location in the optical path selected from the group consisting of the working electrode, the transparent sample window, and any combination thereof.

4. The method of claim 1, wherein the detection species selected from the group consisting of a porphyrin, a metalloporphyrin comprising a metal ion, a metalloporphyrin-protein complex, and any combination thereof.

5. The method of claim 4, wherein the metal ion in the metalloporphyrin is selected from the group consisting of iron(II), iron(III), chromium(II), chromium(III), cobalt(II), cobalt(III), copper(II), lead(II), lead(IV), mercury(I), mercury(II), tin(II), tin(IV), cadmium, zinc, gold(III), manganese(II), manganese(III), manganese(IV), aluminum, nickel(II), nickel(III), antimony(III), antimony(V), vanadium, and any combination thereof.

6. The method of claim 4, wherein the metalloporphyrin-protein complex is selected from the group consisting of hemoglobin, myoglobin, cytochrome, catalase, endothelial nitric oxide synthase, methemoglobin, chlorophyll, isomers thereof, and any combination thereof.

7. The method of claim 1, wherein the conductive fluid is selected from the group consisting of a combination solvent and supporting electrolyte, an ionic fluid, and any combination thereof.

8. The method of claim 1, wherein the output signal is selected from the group consisting of a voltammetry signal, an electromagnetic radiation absorption spectroscopy signal, and any combination thereof.

9. The method of claim 1, wherein the output signal corresponds to a presence and/or absence of an analyte in the sample.

10. The method of claim 9, wherein the analyte is selected from the group consisting of carbon dioxide, hydrogen sulfide, a mercaptan, carbon monoxide, nitric oxide, mercury, and any combination thereof.

11. The method of claim 1, further comprising mixing the conductive fluid, the detection species, and the sample in the spectroelectrochemistry cell, thereby replacing the transparent sample window fluid with a fresh transparent sample window fluid.

12. The method of claim 1, wherein the sample is formation fluid from a subterranean formation.

13. The method of claim 1, wherein the spectroelectrochemistry cell, the potentiostat, the electromagnetic radiation source, and the detector are located in a wellbore in a subterranean formation.

14. The method of claim 13, wherein the spectroelectrochemistry cell, the potentiostat, the electromagnetic radiation source, and the detector are located in the wellbore in the subterranean formation on a tool selected from the group consisting of a measurement-while-drilling wireline, a drill string, a formation tester, a wireline, a drill stem test tool, and any combination thereof.

15. The method of claim 13, wherein the sample is formation fluid from the wellbore in the subterranean formation.

16. The method of claim 1, wherein the spectroelectrochemistry cell, the potentiostat, the electromagnetic radiation source, and the detector are located in a pipeline comprising hydrocarbon fluid.

17. A system comprising:
a spectroelectrochemistry cell comprising:
a cell body that has a first volume,
a transparent sample window defined in the cell body and in fluid communication therewith, the transparent sample window defining an optical path through the cell body and having a second volume,
a working electrode extending through the cell body and into the transparent sample window in the optical path, the working electrode electrically coupled to a working electrical wire lead at a first end thereof,
a counter electrode extending through the cell body, the counter electrode electrically coupled to a counter electrical wire lead at a first end thereof,
a reference electrode extending through the cell body, the reference electrode electrically coupled to a reference electrical wire lead at a first end thereof, and
a fluid mixer located within the cell body;
a potentiostat electrically coupled to a second end of the working electrical wire lead, a second end of the counter electrical wire lead, and a second end of the reference electrical wire lead, wherein the potentiostat applies a voltage potential across the transparent sample window;
an electromagnetic radiation source that emits electromagnetic radiation into the optical path through the transparent sample window, wherein the electromagnetic radiation optically interacts with a transparent sample window fluid to generate modified electromagnetic radiation; and
a detector that receives the modified electromagnetic radiation;
wherein upon introduction of a conductive fluid, a detection species, and a sample into the cell body, a portion of the conductive fluid, the detection species, and the sample enter into the transparent sample window in the optical path, thereby forming transparent sample window fluid;
and upon application of a voltage potential with the potentiostat across the transparent sample window, an electrochemical reaction is driven between the detection species and the sample in the transparent sample window fluid.

18. The system of claim 17, wherein the spectroelectrochemistry cell, the potentiostat, the electromagnetic radiation source, and the detector are located in a wellbore in a subterranean formation.

19. The method of claim 18, wherein the spectroelectrochemistry cell, the potentiostat, the electromagnetic radiation source, and the detector are located in the wellbore in the subterranean formation on a tool selected from the group consisting of measurement-while-drilling wireline, a drill string, a formation tester, a wireline, a drill stem test tool, and any combination thereof.

20. The system of claim 17, wherein the spectroelectrochemistry cell, the potentiostat, the electromagnetic radiation source, and the detector are located in a pipeline comprising hydrocarbon fluid.

* * * * *